US010240981B2

(12) United States Patent
Ross et al.

(10) Patent No.: US 10,240,981 B2
(45) Date of Patent: Mar. 26, 2019

(54) OPTICAL SPECTROMETER CONFIGURATION INCLUDING SPATIALLY VARIABLE FILTER (SVF)

(71) Applicants: Matthew F. Ross, San Diego, CA (US); Scott A. Chalmers, San Diego, CA (US); Randall S. Geels, San Diego, CA (US)

(72) Inventors: Matthew F. Ross, San Diego, CA (US); Scott A. Chalmers, San Diego, CA (US); Randall S. Geels, San Diego, CA (US)

(73) Assignee: Filmetrics, Inc., San Diego, CA (US)

( * ) Notice: Subject to any disclaimer, the term of this patent is extended or adjusted under 35 U.S.C. 154(b) by 250 days.

(21) Appl. No.: 15/367,715

(22) Filed: Dec. 2, 2016

(65) Prior Publication Data

US 2017/0160134 A1    Jun. 8, 2017

Related U.S. Application Data

(60) Provisional application No. 62/261,985, filed on Dec. 2, 2015.

(51) Int. Cl.
| | | |
|---|---|---|
| G01N 21/25 | (2006.01) | |
| G01J 3/26 | (2006.01) | |
| G01J 3/10 | (2006.01) | |
| G01B 11/06 | (2006.01) | |
| G01B 11/24 | (2006.01) | |
| G01N 21/45 | (2006.01) | |
| G01N 21/84 | (2006.01) | |
| G01J 3/12 | (2006.01) | |
| G01J 3/28 | (2006.01) | |

(52) U.S. Cl.
CPC ............ *G01J 3/26* (2013.01); *G01B 11/0625* (2013.01); *G01B 11/0675* (2013.01); *G01B 11/2441* (2013.01); *G01J 3/10* (2013.01); *G01N 21/255* (2013.01); *G01N 21/45* (2013.01); *G01N 21/8422* (2013.01); *G01J 2003/123* (2013.01); *G01J 2003/1243* (2013.01); *G01J 2003/2866* (2013.01); *G01N 2021/8427* (2013.01)

(58) Field of Classification Search
CPC ........ G01J 3/28; G01J 3/30; G01J 3/38; G01J 3/02; G01J 3/12; G01J 3/26; G02F 1/167; G01N 21/27
See application file for complete search history.

(56) References Cited

U.S. PATENT DOCUMENTS 6,371,662 B1 *   4/2002   Leard .................... H01S 5/0687
                                                                              359/888
6,657,758 B1 * 12/2003   Garner ................. B01J 19/0046
                                                                              359/196.1

* cited by examiner

*Primary Examiner* — Abdullahi Nur
(74) *Attorney, Agent, or Firm* — IPR Law Group PC (57) ABSTRACT

A system comprising a light source configured to illuminate a sample under measurement. The system includes a detector configured to receive reflected light from the sample, and the detector generates a signal representing the reflected light. A spatially variable filter (SVF) is positioned in the optical path. The SVF is configured to have spectral properties that vary as a function of illuminated position on the SVF.

63 Claims, 4 Drawing Sheets

OPTICAL SPECTROMETER CONFIGURATION INCLUDING SPATIALLY VARIABLE FILTER (SVF)

RELATED APPLICATIONS

This application claims the benefit of U.S. Patent Application Ser. No. 62/261,985, filed Dec. 2, 2015.

This application is related to U.S. patent application Ser. Nos. 13/742,782 and 13/743,210, both filed Jan. 16, 2013.

TECHNICAL FIELD

This invention relates generally to the field of optical instrumentation.

BACKGROUND

Optical instrumentation used in spectroscopy has long relied on conventional filter technologies to generate light for measurement operations. However, these conventional technologies limit tunability of these instrumentation systems.

INCORPORATION BY REFERENCE

Each publication, patent, and/or patent application mentioned in this specification is herein incorporated by reference in its entirety to the same extent as if each individual publication, patent and/or patent application was specifically and individually indicated to be incorporated by reference.

BRIEF DESCRIPTION OF THE DRAWINGS

The components in the figures are not necessarily to scale, emphasis instead being placed upon illustrating the principles of the embodiments. In the figures, like reference numerals designate corresponding parts throughout the different views.

DETAILED DESCRIPTION

Electro-optical systems including fully tunable instrumentation comprising one or more spatially variable filters (SVFs) are described herein. A spatially variable filter (SVF) is an optical interference filter having spectral properties that vary as a function of position (e.g., linear, parabolic, etc.) on the filter, compared to a conventional optical filter with spectral functionality configured to be identical at any location or point on the filter. In the following description, numerous specific details are introduced to provide a thorough understanding of, and enabling description for, embodiments herein. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

A system comprising a light source configured to illuminate a sample under measurement. The system includes a detector configured to receive reflected light from the sample, and the detector generates a signal representing the reflected light. A spatially variable filter (SVF) is positioned in the optical path. The SVF is configured to have spectral properties that vary as a function of illuminated position on the SVF.

Figure 1:
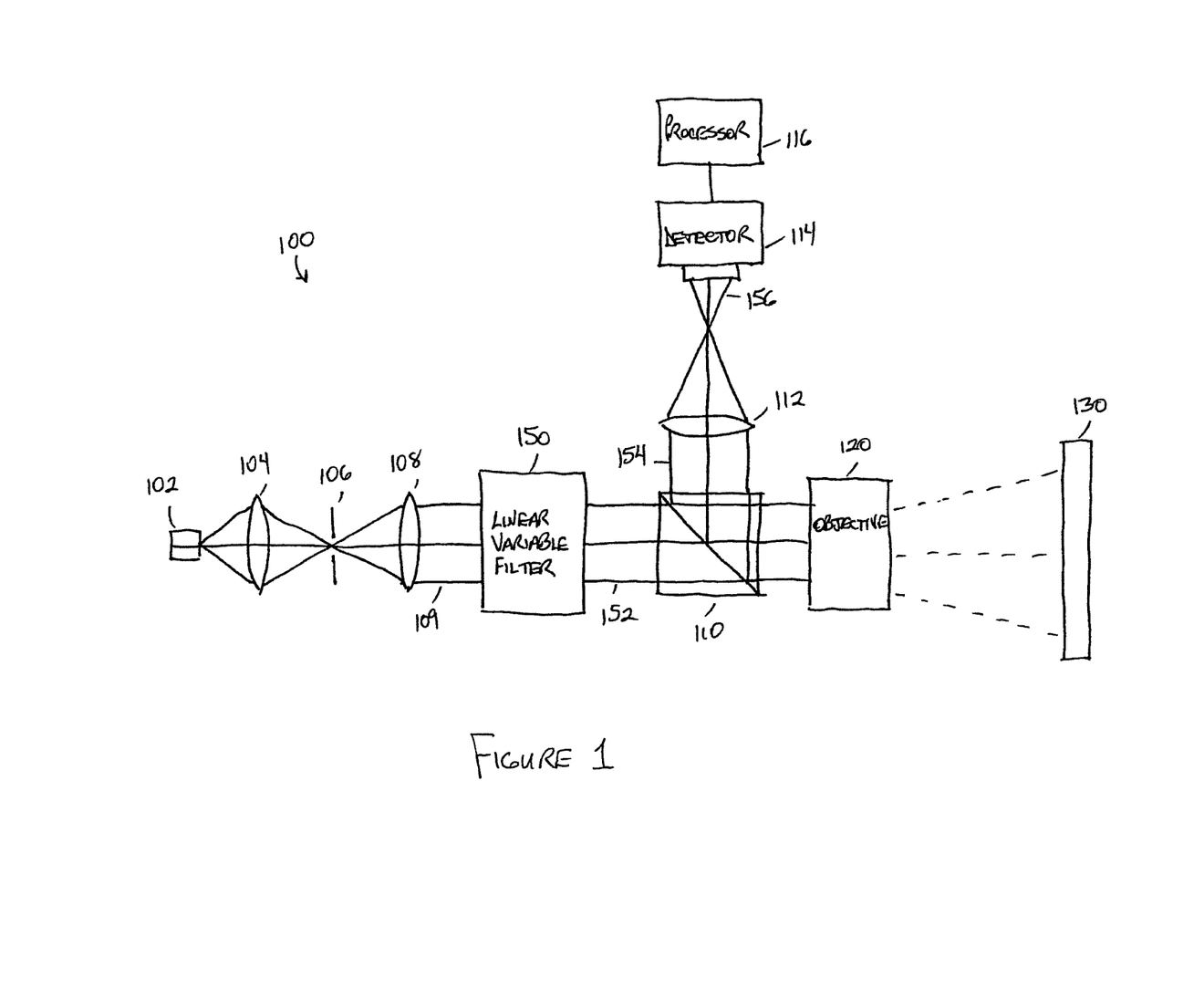
FIG. 1 is a block diagram of an electro-optical system for measuring a layer thickness of a sample, under an embodiment.

FIG. 1 is a block diagram of an electro-optical system 100 for measuring a layer thickness of a sample, under an embodiment. Embodiments of the electrical-optical system described herein include measurement instruments that detect the thickness of the outer layer of a sample (e.g., silicon wafer, etc.). The instruments include a light source forming an aperture image. The light source (e.g., white light, Xenon lamp, Halogen lamp, laser, etc.) of an embodiment includes a radiation source 102, a condensing lens 104, a circular aperture 106, a collimator lens 108. The instruments include a spatially variable filter (SVF) 150, which in this example embodiment is a linear variable filter (LVF) 150, and an objective 120. A monochromatic beam generated by this optical configuration illuminates the surface of the sample 130 (when present) with collimated light. The light emitted or reflected from the surface of the sample 130 returns through the objective 120 and forms an aperture image on an optical device 110, which redirects the image to a detector 114 (e.g., charge coupled device (CCD) camera, complementary metal-oxide semiconductor (CMOS) camera, etc.). The image is converted to a map of measured reflectance data by a processor 116. This map of measured reflectance data is then compared to reference reflectance data to generate a map of the outer layer thickness profile of the sample 130. For purposes of the description herein, the measurement of an outer layer of a sample 130 (e.g., silicon on insulator (SOI) on silicon, SiO2 on silicon, etc.) comprising a semiconductor wafer is described, but the embodiments are not so limited.

An example embodiment includes a white light source comprising a circular aperture 106 illuminated by a Xenon or Halogen lamp 102 and a condensing lens 104. Light passing through aperture 106 impinges on a collimator lens 108 to form a beam 109 of collimated light. The size of the aperture 106, which is selected as appropriate to a configuration of the system 100, determines the field angles in the collimated light sections of the optical system and the orientation is chosen to allow an aperture image to be projected onto the sample 130. Alternatively, the condensing lens 104 may be replaced by a fiber optic light guide but is not so limited.

The light source from the collimator lens 108 is input to a linear variable filter (LVF) where it is filtered to produce a corresponding series of collimated monochromatic light beams 152 at an output of the LVF. LVF configurations of embodiments include one or more LVFs, as described in detail herein. The wavelengths of these collimated monochromatic light beams 152 range from approximately 300 nm to 850 nm but are not so limited. The LVF is described in detail herein.

An interferometry objective 120 receives the collimated monochromatic light beams 152 from the LVF output and forms interference images on the surface of the sample 130. Changing the relative positioning between the interferometry objective 120 and the sample results in interference images at a sequence of phase differences; changes in the relative positioning can be realized by changing a position of the interferometry objective 120 relative to the sample and/or changing a position of the sample relative to the interferometry objective 120. These interference maps, which are functions of background intensity, fringe modulation, and phase, provide information or data from which the topographic image of the sample is derived. The interferometry objective 120 of an embodiment includes an interferometry objective (e.g., Mirau, Michelson, etc.) available from Nikon Corporation, but is not so limited.

A collimated light image of the interference fringe pattern is reflected off the surface of the sample 130 and returned through the objective 120. The objective 120 projects a condensed image of the reflected fringe pattern upon the optical device 110, which includes an optical device configured as a reflector 110. The reflector 110 of an embodiment includes a beam splitter, but is not so limited. Alternatively, the reflector 110 includes an off-axis reflector (not shown). The reflector 110 receives a collimated fringe pattern image from the objective 120 and reflects a portion 154 of this collimated beam to a final collimator lens 112. The final collimator lens 112 projects a beam 156 comprising an image of the fringe pattern onto a detector 114 (e.g., CCD camera detector array, etc.). The detector 114 is coupled or connected to a processor 116 configured to process data of the detector.

Generally, as described above, a spatially variable filter (SVF) is an optical interference filter having varying spectral functionality along one direction of the filter, compared to a conventional optical filter with spectral functionality configured to be identical at any location of the filter. While the example embodiments described herein include an SPV that is a linear variable filter (LVF), the embodiments are not limited to LVFs but instead can include any type of SVF as appropriate to a configuration of the system.

The term "linear" in LVF relates to the spectral properties that vary generally linearly, thereby making the wavelength variation a linear function of the position on the filter. The wavelength variation of an embodiment is achieved by an interference coating that is wedged or graduated in one direction, creating a linear shift of the center or edge wavelength along the same direction of the filter. The LVFs of example embodiments are rectangular types where the wavelength characteristic changes along the longitudinal direction, but are not so limited. The LVFs of alternative example embodiments include circular variable filters for which the variation is obtained by rotating the filters. In other alternative configurations, tunability of the LVF is obtained by changing the angle of incidence.

A single LVF can replace one or more dedicated filters in an optical instrument, and each LVF is configured to adjust the position of the edge by sliding the filter. The LVFs are coated on single quartz substrates for minimal auto-fluorescence and high laser damage threshold, and are coated with ultra-hard surface coatings (UHC), but are not so limited. In contrast to conventional absorptive or induced transmission filters and soft coated filters, which are susceptible to damage when used with high power sources, the LVFs of an embodiment include a hard-coating non-absorbing technology, such as all-dielectric metal-oxides and quartz constructions, that withstand damage by high optical power sources. Furthermore, the high precision multi-layer coatings provide very high edge steepness along with around 90 percent transmission efficiency and typically better than 40 dB out-of-band suppression.

The LVF of an embodiment includes a combination of long-wave pass and short-wave pass interference filters. More particularly, this combination LVF configuration includes a Linear Variable Short Wave Pass filter (LVSWP) and a Linear Variable Long Wave Pass filter (LVLWP) to realize a variable band-pass filter. The variable band-pass filter can be scanned synchronously with the wavelength selected by the relative positioning of the LVSWP/LVLWP to severely reduce the influence of higher order effects and stray light, thus improving the performance of the spectrometers of an embodiment.

The filters of embodiments including the combined LVF configuration (LVSWP and LVLWP) operate in a spectral range from 300 nm to 850 nm, but are not so limited. In general, interference filters have a number of advantages in selecting passbands or rejection of various wavelengths. The two most prominent advantages being that the spectral shape and the grade of rejection are designable. They can comprise up to approximately 150 stacked layers of thin films of varying optical thickness "nd", where variable "n" represents refractive index and variable "d" represents thickness of the film. It is thus possible to create a variable long-wave pass filter by varying the layer thickness along the filter by a linear wedge. Likewise a short-wave pass filter can be constructed by using the short wave cut-off of the quarter wave stack and again modifying thicknesses to give a uniform transmission over a wavelength range limited in this case by the arrival of second order interference effects.

The variable-wavelength filter stage of an embodiment combines the LVSWP and the LVLWP filters with a motorized translation stage, which is controlled by software to be driven synchronously with the diffraction grating of the monochromator. Thus, when properly calibrated, the filters are always positioned in the beam path in such a way that the wavelength selected by the grating lies near the cut-off wavelength of the respective filter, while still in the region of maximum transmission. In the case of the LVLWP, the very sharp edge and strong reflection then eliminates any stray light at wavelengths shorter than the cut-off. Depending upon the nature of the measurements and the sensitivity to scattered light, an embodiment combines the LVLWP with the LVSWP to create a band-pass filter realizing finely tunable bandwidths as small as the order of 25 nm without loss in maximum transmission.

Each of the filters can be used separately, and combining the LVLWP and LVSWP realizes band-pass filters that can be tuned continuously with center wavelengths from approximately 300 nm to 850 nm, with the added benefit of tunable bandwidth. The LVF configuration provides enhanced transmission level and edge steepness, and the filters offer blocking better than OD3 over the complete reflection range (blocking can be increased to beyond OD5 by placing another linear variable filter in series).

Referring to FIG. 1, the LVF 150 of the system 100 includes a single tunable bandpass LVF for which the output wavelength is selected according to the spatial position illuminated on the filter. The bandpass LVF is configured by combining two edgepass LVFs, one LVLWP and one LVSWP, to create a tunable pass band. By moving both filters together relative to each other, the central wavelength can be continuously adjusted and by moving them relative to one another the bandwidth of the filter can also be tuned. In imaging applications this enables optimization of the filter to maximize efficiency of the imaging. Using two of these fully tunable LVF bandpass filters together, because the LVFs have intrinsically high transmission efficiency, enables maximum tunable power from a light source 102 including a supercontinuum light source 102. The LVFs as described herein are available from Delta Optical Thin Film A/S, for example, but are not so limited.

Figure 2:
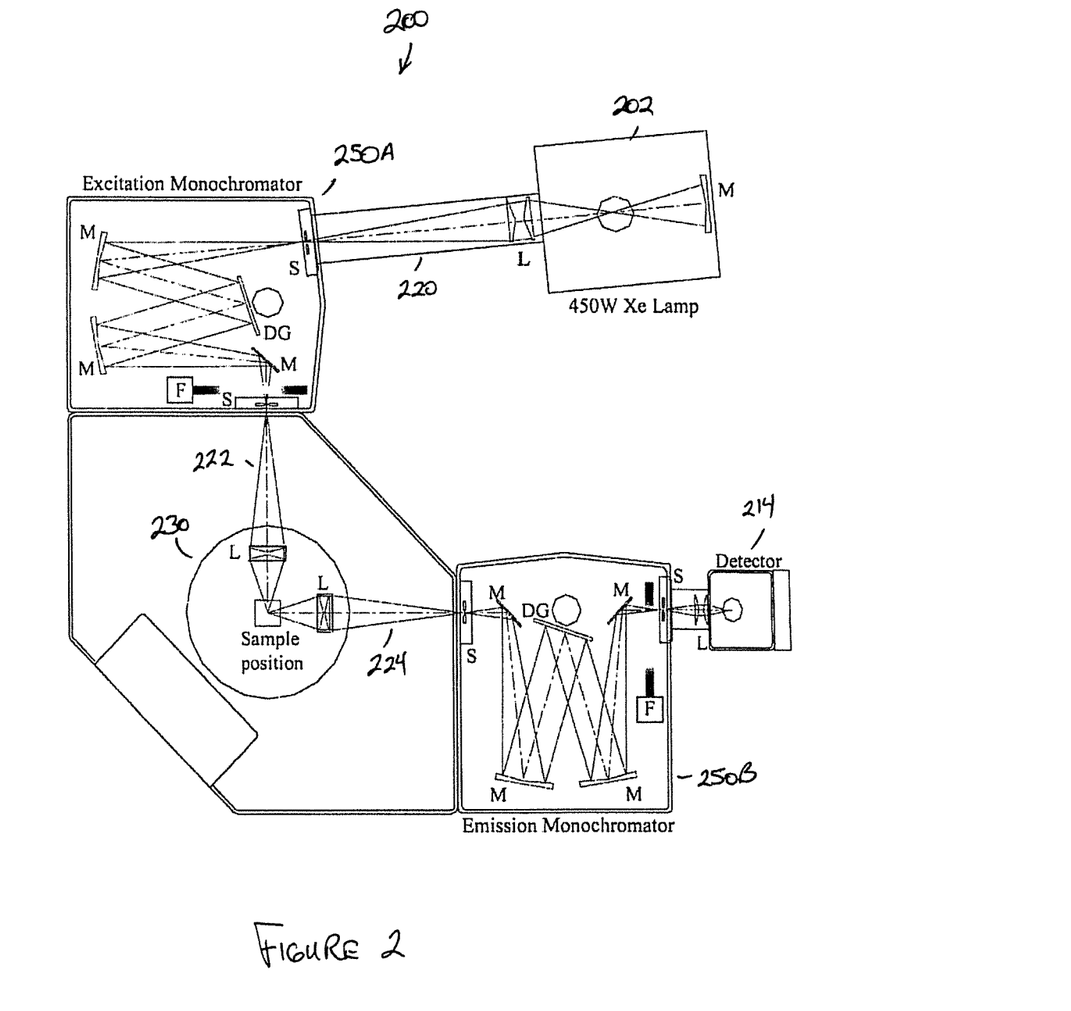
FIG. 2 is a block diagram of an optical system configuration having two linear variable filters (LVFs) positioned at different points in the optical path, under an embodiment.

The bandpass LVF described herein can include two separate LVFs positioned at different points in the optical path. Generally, FIG. 2 is a block diagram of an optical system 200 configuration having two linear variable filters (LVFs) 250A, 250B positioned at different points in the optical path, under an embodiment. This example configuration includes a light source 202 (e.g., 450 Watt Xenon Lamp, etc.) optically coupled 220 to the input of a first LVF 250A (e.g., excitation monochromator). The output of the first LVF 250A is optically coupled via an excitation optical path 224 to a stage 230 configured to receive and secure a sample under test. The emission optical path 224 from the stage 230 is optically coupled to the input of a second LVF 250B (e.g., emission monochromator). The output of the second LVF 250B is optically coupled 226 to the detector 214. One or more of the optical path 220 from the light source, the excitation optical path 224, the emission optical path 224, and the optical path 226 to the detector 214 includes a lens L configuration as appropriate to the configuration of the system 200.

The first LVF 250A and the second LVF 250B of an embodiment operate in combination to provide the LVF bandpass filter. The first LVF 250A includes a slit S, numerous mirrors M, a diffraction grating DG, and a variable filter stage F, as appropriate to the configuration of the system 200. Likewise, the second LVF 250B includes a slit S, numerous mirrors M, a diffraction grating DG, and a variable filter stage F, as appropriate to the configuration of the system 200.

In an embodiment of the LVF bandpass filter, the variable filter stage F of the first LVF 250A is configured as a linear variable long wave pass filter (LVLWP) and the variable filter stage F of the second LVF 250B is configured as a linear variable short wave pass filter (LVSWP). In an alternative embodiment of the LVF bandpass filter, the variable filter stage F of the first LVF 250A is configured as a linear variable short wave pass filter (LVSWP) and the variable filter stage F of the second LVF 250B is configured as a linear variable long wave pass filter (LVLWP).

A configuration of the LVSWP filter of an embodiment includes but is not limited to the following: edge tuned from 320 nm-850 nm, blocking up to 684 nm when edge at lowest wavelength (relatively lower near-edge blocking, relatively higher UV transmittance); edge tuned from 320 nm-850 nm, blocking up to 684 nm when edge at lowest wavelength (relatively deeper near-edge blocking, relatively lower UV transmittance.

A configuration of the LVLWP filter of an embodiment includes but is not limited to the following: edge tuned from 310 nm-850 nm, blocking down to 340 nm when edge at highest wavelength (relatively less steep edge and narrower blocking range); edge tuned from 310 nm-850 nm, blocking down to 190 nm when edge at highest wavelength (relatively steeper edge and broader blocking range).

Regarding bandpass filter configurations, embodiments may include but are not limited to different Linear Variable Bandpass Filters as follows: center wavelength range 450 nm to 880 nm, bandwidth approximately 2% of center wavelength, transmission 60% to 90%, blocking range 200 nm to 1150 nm, blocking level OD4, size 24 mm×36 mm; center wavelength range 450 nm to 850 nm, bandwidth approximately 4% of center wavelength, transmission 70% to 90%, blocking range 200 nm to 1100 nm, blocking level OD4, size 25 mm×25 mm; center wavelength range 800 nm to 1000 nm, bandwidth approximately 0.6% of center wavelength, transmission >70%, blocking range 200 nm to 1200 nm, blocking level OD4, size 19 mm×8 mm; center wavelength range 800 nm to 1000 nm, bandwidth approximately 1% of center wavelength, transmission >70%, blocking range 200 nm to 1200 nm, blocking level OD4, size 19 mm×8 mm.

Figure 3:
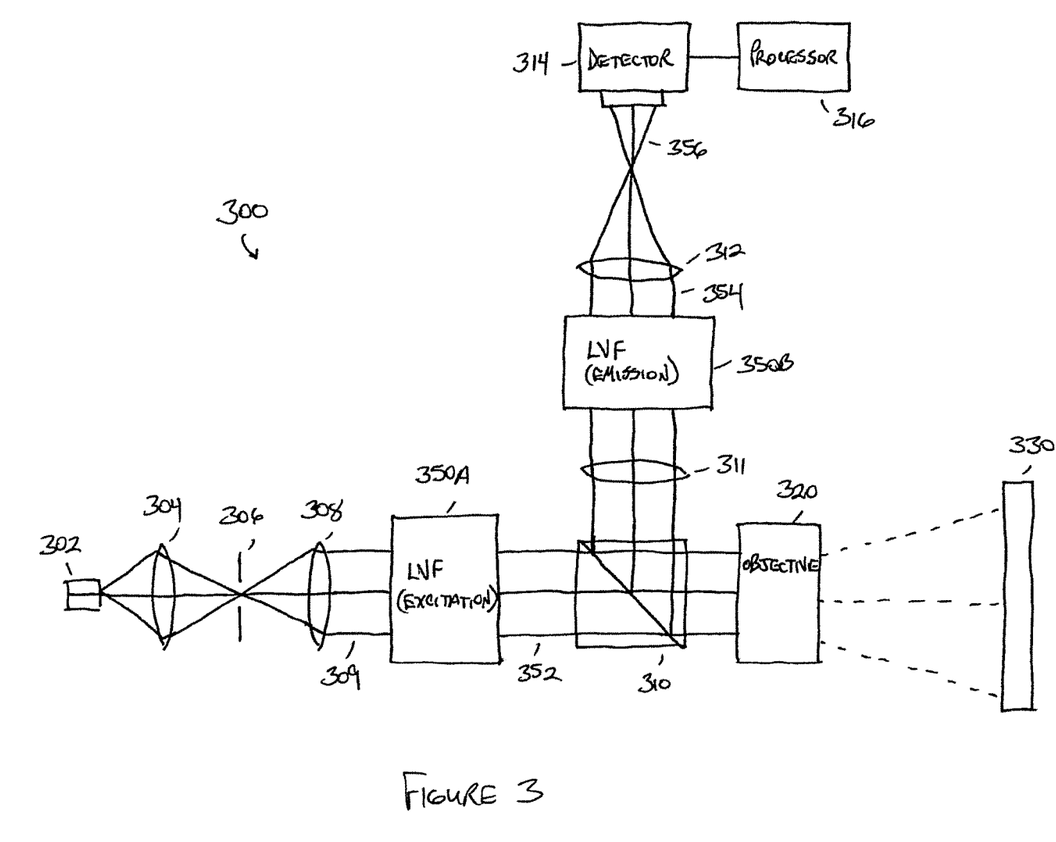
FIG. 3 is another block diagram of an optical system configuration having two linear variable filters (LVFs) positioned at different points in the optical path, under an embodiment.

More specifically, FIG. 3 is another block diagram of an optical system configuration 300 having two linear variable filters (LVFs) 350A, 350B positioned at different points in the optical path, under an embodiment. The configuration of the electrical-optical system includes a light source comprising an aperture 306 illuminated by a lamp 302 and a condensing lens 304. Light passing through aperture 306 impinges on a collimator lens 308 to form a beam 309 of collimated light. The size of the aperture 306 determines the field angles in the collimated light sections of the optical system and the orientation is chosen to allow an aperture image to be projected onto the sample 330. Alternatively, the condensing lens 304 may be replaced by a fiber optic light guide but is not so limited.

The light source from the collimator lens 308 is input to a first LVF 350A (excitation) where it is filtered to produce a corresponding series of collimated monochromatic light beams 352 at an output of the first LVF 350A. The wavelengths of these collimated monochromatic light beams 352 range from approximately 300 nm to 850 nm but are not so limited. The configuration of the first LVF 352 is described in detail herein.

An interferometry objective 320 receives the collimated monochromatic light beams 352 from the output of the first LVF 350A and forms interference images on the surface of the sample 330. Changing the relative positioning between the interferometry objective 320 and the sample results in interference images at a sequence of phase differences; changes in the relative positioning can be realized by changing a position of the interferometry objective 320 relative to the sample and/or changing a position of the sample relative to the interferometry objective 320. These interference maps, which are functions of background intensity, fringe modulation, and phase, provide information or data from which the topographic image of the sample is derived.

A collimated light image of the interference fringe pattern is reflected from the surface of the sample 330 and returned through the objective 320. The objective 320 projects a condensed image of the reflected fringe pattern upon a reflector 310. The reflector 310 of an embodiment includes a beam splitter, but is not so limited. The reflector 310 is configured to redirect the reflected fringe pattern image from the sample 330 to a collimator lens 311. The light source from the collimator lens 311 is input to a second LVF 350B (emission) where it is filtered to produce a corresponding series of collimated light beams 354 at an output of the second LVF 350B. The wavelengths of these collimated light beams 354 range from approximately 300 nm to 850 nm but are not so limited.

The first LVF 350A and the second LVF 350B of an embodiment operate in combination to provide the LVF bandpass filter. In an embodiment of the LVF bandpass filter, the first LVF 350A is configured as a linear variable long wave pass filter (LVLWP) and the second LVF 350B is configured as a linear variable short wave pass filter (LVSWP). In an alternative embodiment of the LVF bandpass filter, the first LVF 350A is configured as a linear variable short wave pass filter (LVSWP) and the second LVF 350B is configured as a linear variable long wave pass filter (LVLWP).

The output of the second LVF 350B is optically coupled to final collimator lens 312, which is configured to project a collimated beam 356 comprising an image of the fringe pattern onto a detector 314 (e.g., CCD camera detector array, etc.). The detector 314 is coupled or connected to a processor 316 configured to process data of the detector.

The LVF of an alternative embodiment includes the LVLWP and the corresponding LVSWP, as described herein, and optionally a Linear Variable Dichroic. The dichroic filter, or interference filter, is an accurate color filter used to selectively pass light of a small or limited range of colors while reflecting other colors. Embodiments may include a dichroic filter or slide having an edge tuned from 320 nm-760 nm. A dichroic filter as described herein is available from Delta Optical Thin Film A/S, for example, but is not so limited. Alternative embodiments can include order-sorting filters for filtering higher orders of diffractive optics and suppression of background noise.

Figure 4:
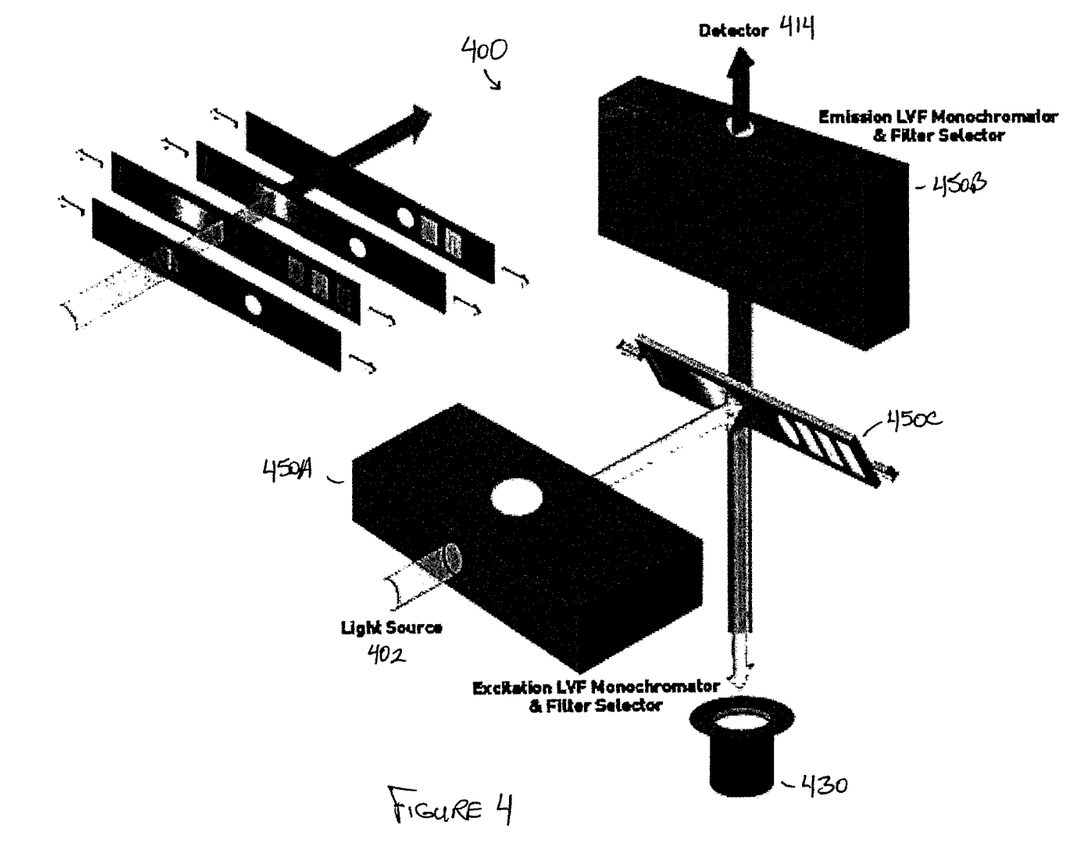
FIG. 4 is a block diagram of an electro-optical system configured with two LVFs and a dichroic filter, under an alternative embodiment.

FIG. 4 is a block diagram of an electro-optical system 400 configured with two LVFs 450A, 450B and a dichroic filter 450C, under an alternative embodiment. The light source 402 of this embodiment is optically coupled to the first LVF 450A (excitation) where it is filtered to produce a corresponding series of collimated monochromatic light beams at an output of the first LVF 450A. The light output of the first LVF 450A is optically coupled to the dichroic filter 450C, and then optically coupled from the dichroic filter 450C to the sample 430. The dichroic filter 450C of this example embodiment is configured and/or positioned for use as a reflector (e.g., see FIG. 3), or beam splitter, but the embodiment is not so limited. Light emitted or reflected from the surface of the sample 430 is optically coupled to an input of a second LVF 450B (emission) via the dichroic filter 450C. The second LVF 450B is configured to filter the received light signal to produce a corresponding series of collimated monochromatic light beams at an output of the second LVF 450B. The output of the second LVF 450B is optically coupled to a detector 414 as described in detail herein. Additional elements of the electro-optical system 400 are as appropriate to the configuration of the system 400 as described in detail herein.

The first LVF 450A and the second LVF 450B of an embodiment operate in combination to provide the LVF bandpass filter. In an embodiment of the LVF bandpass filter, the first LVF 450A is configured as a linear variable long wave pass filter (LVLWP) and the second LVF 450B is configured as a linear variable short wave pass filter (LVSWP). In an alternative embodiment of the LVF bandpass filter, the first LVF 450A is configured as a linear variable short wave pass filter (LVSWP) and the second LVF 450B is configured as a linear variable long wave pass filter (LVLWP).

As described herein, the collimated beam formed by the final collimator lens includes an image of the reflected fringe pattern. This image is projected upon and captured by the detector, which as an example includes but is not limited to a CCD camera detector array. The detector and/or a processor coupled or connected to the detector generate a reflectance map by digitizing the detector signals corresponding to the projected fringe pattern image. This raw reflectance data may be normalized to eliminate variations in pixel sensitivity and may be reduced in size by averaging signals over blocks of pixels to match the spatial limitations of the subsequent chemical micropolishing process. In determining the thickness of an outer silicon layer (e.g., silicon on insulator (SOI) on silicon, SiO2 on silicon, etc.) of a sample that is a silicon wafer, either a numerical computation method or a SOI calibration wafer may be used, but the embodiments are not so limited.

A numerical method of determining SOI thickness includes assuming values for the thin film constants and calculating spectral reflectances for a set of wavelengths corresponding to the monochromatic light produced by the filtered white light source. This calculation is performed for a number of different SOI thicknesses, and provided that the initial thin film constant assumptions are correct should only need to be computed once. This calculation provides sets of reflectance values for thicknesses ranging from the thinnest to the thickest estimated value of the SOI. These computed spectral reflectances are then compared with the measured reflectance data at specific points on the wafer using a root mean square (RMS) merit function. This merit function is evaluated for different values of thickness until a minimum or best match is found, which in turn indicates the most likely thickness. Alternative pattern matching merit functions can be used in alternative embodiments.

An alternative method of determining SOI thickness comprises generating a set of spectral reflectances from an SOI calibration wafer containing a stepped outer surface, where each square area of the wafer has a different known SOI thickness. This wafer can be calibrated for SOI thicknesses down to zero silicon thickness by using a stylus profilometer. The calibration wafer is manufactured from the same batch of materials and is subject to the same manufacturing conditions as the wafer under measurement. Consequently, the intrinsic optical properties of the calibration wafer such as the absorption coefficient and the index of refraction, and also the dispersive behavior should match those of the wafer being tested.

The spectral reflectances of the calibration wafer are obtained by subjecting this wafer to the measuring method of the present invention. These spectral reflectances are stored in the computer and are used as a reference for comparison with the spectral reflectances of a measured SOI wafer. The calibration wafer has reference reflectances for numerous different SOI thicknesses and the reference reflectance that most closely matches the reflectance at any point on the surface of the measured SOI wafer 24 indicates the SOI thickness at that point.

The electro-optical system of an embodiment is configured for use with various types of light sources (e.g., white light, laser, xenon lamp, halogen lamp, light emitting diode (LED), etc.), as described in detail herein. For example, the source in an embodiment is a supercontinuum source. Supercontinuum generation is a process in which laser light is converted to light with a very broad spectral bandwidth (i.e., low temporal coherence), whereas the spatial coherence usually remains high. The spectral broadening is generally accomplished by propagating optical pulses through a strongly nonlinear device. For example, an intense (amplified) ultrashort pulse is directed through a piece of bulk glass. Alternatively, pulses can be sent having much lower pulse energy through an optical fiber, having a much higher nonlinearity and also a waveguide structure which ensures a high beam quality.

The supercontinuum source of an embodiment is used in combination with a high power transmission filter but is not so limited. An example of the high power transmission filter is the SuperChrome filter, available from Fianium. The SuperChrome filter is a single-channel transmission filter, which allows the user to both select the wavelength and tune the bandwidth of a supercontinuum source. The filter operates over the entire visible spectrum from below 400 nm to greater than 850 nm. This filter offers a typical transmission of greater than 80%, with maximum performance achieved using filter bandwidths ranging from 8 nm to more than 50 nm, for example. When the filter is coupled to a supercontinuum source (e.g., Fianium SC400, SC450, SC 480, etc.), more than 100 mW of power, tunable across the visible range, is available in a 25 nm bandwidth. The unit provides levels of out of band suppression of approximately 40 dB. SuperChrome filter enhances the flexibility of the supercontinuum laser output offering a tunable laser source at any user-defined wavelength.

The light source of an alternative embodiment includes a broadband light source, which in an example includes the broadband light source described in U.S. patent application Ser. No. 13/742,782. The broadband light source efficiently combines the light from one or more LEDs with a low-color-temperature incandescent lamp, thereby realizing a high-lifetime broadband light source suitable for low-power applications. As an example, the light-combining apparatus that combines light from a white-light LED with light from a low-color-temperature incandescent lamp using a fiber-optic coupler. The apparatus includes a two-input fiber optic coupler coupled to a white-light LED and a low-color-temperature incandescent lamp. The fiber-optic coupler of an embodiment is a dual-branch fiber-optic light guide available from Edmund Optics (part number NT54-199), or a fused coupler such as those available from OZ Optics, but is not so limited.

In this embodiment, the output of white-light LED and the output of low-color-temperature incandescent lamp are directed into the two input legs of the two-input fiber optic coupler. The resultant spectrum emitting from the fiber-optic coupler is the combined spectral output of the white-light LED source and the low-color-temperature incandescent lamp source. The output emitted from the fiber-optic coupler is optically coupled to the linear variable filter (LVF) as described in detail herein.

The electro-optical systems described herein are calibrated before and during measurement operations using various conventional calibration procedures. As an example, the calibration process of an embodiment includes a real-time calibration as described in U.S. patent application Ser. No. 13/743,210. Embodiments of this calibration process include an apparatus that injects light from a calibration source into the spectrometer. The calibration system generally includes a calibration light source, or calibration source, coupled between an output of a controller and an input of a spectrometer. In this embodiment, a neon lamp is the calibration light source, but the embodiment is not so limited. The calibration light source is controlled (turned on and off) by the controller. The output of the calibration light source is collected by a calibration optical fiber and transmitted to an input slit of the spectrometer. The spectrometer receives the light that it is to measure, referred to herein as the light-under-test, via a spectrometer-input optical fiber that is coupled between the light-under-test and the spectrometer.

Generally, the spectrometer calibration of this embodiment comprises coupling a calibration light source to an input slit of a spectrometer using a calibration optical fiber. The method includes, in addition to the calibration optical fiber, coupling an input optical fiber to the input slit of the spectrometer. The input optical fiber is coupled to a light-under-test. The method includes activating the calibration light source and simultaneously minimizing the light-under-test. The method includes acquiring a calibration spectrum from the spectrometer. The calibration spectrum results from light output of the calibration light source being received at the spectrometer. Using the calibration spectrum, the method includes generating a set of calibration coefficients.

Embodiments include a system comprising a light source, and a retention device configured to receive and retain a sample for measurement. The system includes a detector configured to receive reflected light from the sample. The detector generates a signal representing the reflected light. An optical path is defined by the light source, the sample when present, and the detector. The system includes a spatially variable filter (SVF) positioned in the optical path. The SVF is configured to have spectral properties that vary as a function of illuminated position on the SVF.

Embodiments include a system comprising: a light source; a retention device configured to receive and retain a sample for measurement; a detector configured to receive reflected light from the sample, wherein the detector generates a signal representing the reflected light, wherein an optical path is defined by the light source, the sample when present, and the detector; and a spatially variable filter (SVF) positioned in the optical path, wherein the SVF is configured to have spectral properties that vary as a function of illuminated position on the SVF.

The SVF includes a linear variable filter (LVF), wherein the LVF is configured to have spectral properties that vary linearly with position along a direction of the LVF.

Output illumination of the LVF includes a wavelength that varies as a linear function of a position of input illumination on the LVF.

The LVF is configured so a spatial position illuminated on the LVF selects an output wavelength of the LVF.

The LVF comprises a substrate including an interference coating that is graduated along a direction of the LVF.

A position of the LVF relative to the light source is configured as variable, wherein the LVF is scanned with the light source.

An output of the LVF includes a series of collimated monochromatic light beams.

The output of the LVF includes light having a wavelength approximately in a range of 300 nanometers (nm) to 850 nm.

The LVF is tunable.

The LVF includes a variable pass band filter comprising a short wave pass component and a long wave pass component.

The short wave pass component includes a first LVF and the long wave pass component includes a second LVF.

The short wave pass component is positioned adjacent the long wave pass component.

A first position of at least one of the short wave pass component and the long wave pass component is adjusted relative to a second position of the other of the short wave pass component and the long wave pass component, wherein a pass band of the LVF is determined by the first position and the second position.

A translation stage configured to control at least one of the first position and the second position.

The SVF includes a circularly variable filter (CVF), wherein the CVF is configured to have spectral properties that vary with position along an arc of the CVF.

The SVF is tunable.

A position of the SVF in the optical path includes a first region between the light source and the retention device.

The system includes a dichroic filter in the first region.

A position of the SVF in the optical path includes a second region between the detector and the retention device.

The system includes a dichroic filter in the second region.

The SVF includes a first SVF component and a second SVF component.

The first SVF component includes a short wave pass component and the second SVF component includes a long wave pass component.

The first SVF component includes a long wave pass component and the second SVF component includes a short wave pass component.

A position of the first SVF component includes a first region of the optical path between the light source and the retention device, and a position of the second SVF component includes the first region.

A position of the first SVF component includes a second region of the optical path between the detector and the retention device, and a position of the second SVF component includes the second region.

A position of the first SVF component includes a first region of the optical path between the light source and the retention device.

A position of the second SVF component includes a second region of the optical path between the detector and the retention device.

The system includes a dichroic filter adjacent at least one of the first SVF component and the second SVF component.

The system includes a dichroic filter.

The system includes an optical objective adjacent the retention device, wherein a position of the optical objective relative to the sample when present is variable.

The optical objective is configured to at least one of couple light from the light source onto a surface of the sample when present and couple light reflected from the surface to an input of the detector.

The system includes an optical director positioned in the optical path, wherein the optical director is configured to at least one of couple light from the light source to the sample when present and couple reflected light from the sample when present to the detector.

The optical director comprises at least one of a plurality of mirrors, a beamsplitter, a reflector, and an off-axis reflector.

The optical director comprises a beamsplitter.

The system includes a condensing device in the optical path between the light source and the retention device.

The system includes a collimator device in at least one of a first region of the optical path between at least one of the light source and the retention device and a second region of the optical path between the detector and the retention device.

The system includes a fiber optic light guide in at least one of a first region of the optical path between at least one of the light source and the retention device and a second region of the optical path between the detector and the retention device.

The system includes an aperture in at least one of a first region of the optical path between at least one of the light source and the retention device and a second region of the optical path between the detector and the retention device.

The detector comprises a spectrometer.

The detector comprises a processing device configured to generate reflectance data representing a surface of the sample when present.

Embodiments include a system comprising a light source, and a retention device configured to receive and retain a sample for measurement. The system includes a detector configured to receive reflected light from the sample. The detector generates a signal representing the reflected light. An optical path is defined by the light source, the sample when present, and the detector. The system includes a plurality of spatially variable filters (SVFs) positioned in the optical path. Each SVF of the plurality of SVFs is configured to have spectral properties that vary as a function of illuminated position on the SVF.

Embodiments include a system comprising: a light source; a retention device configured to receive and retain a sample for measurement; a detector configured to receive reflected light from the sample, wherein the detector generates a signal representing the reflected light, wherein an optical path is defined by the light source, the sample when present, and the detector; and a plurality of spatially variable filters (SVFs) positioned in the optical path, wherein each SVF of the plurality of SVFs is configured to have spectral properties that vary as a function of illuminated position on the SVF.

Embodiments include a system comprising a light source, and a retention device configured to receive and retain a sample for measurement. The system includes a detector configured to receive reflected light from the sample. The detector generates a signal representing the reflected light. An optical path is defined by the light source, the sample when present, and the detector. The system includes a spatially variable filter (SVF) including a short wave pass component and a long wave pass component. The SVF is positioned in the optical path. The SVF is configured to have spectral properties that vary as a function of illuminated position on the SVF.

Embodiments include a system comprising: a light source; a retention device configured to receive and retain a sample for measurement; a detector configured to receive reflected light from the sample, wherein the detector generates a signal representing the reflected light, wherein an optical path is defined by the light source, the sample when present, and the detector; and a spatially variable filter (SVF) including a short wave pass component and a long wave pass component, wherein the SVF is positioned in the optical path, wherein the SVF is configured to have spectral properties that vary as a function of illuminated position on the SVF.

Embodiments include a method comprising configuring an optical path to couple light between a light source, a sample when present, and a detector. The method includes configuring a spatially variable filter (SVF) to pass light having spectral properties that vary as a function of a position of illumination on the SVF. The method includes configuring the optical path to include the SVF in at least one position to control properties of at least one of the light and the reflected light. The method includes configuring the detector to receive reflected light from the sample when present and to generate from the reflected light a signal representing a surface of the sample when present.

Embodiments include a method comprising: configuring an optical path to couple light between a light source, a sample when present, and a detector; configuring a spatially variable filter (SVF) to pass light having spectral properties that vary as a function of a position of illumination on the SVF; configuring the optical path to include the SVF in at least one position to control properties of at least one of the light and the reflected light; and configuring the detector to receive reflected light from the sample when present and to generate from the reflected light a signal representing a surface of the sample when present.

The method comprises configuring the SVF to include a linear variable filter (LVF), wherein the LVF is configured to have spectral properties that vary linearly with position along a direction of the LVF.

The method comprises configuring the LVF as tunable, wherein output illumination of the LVF includes a wavelength that varies as a linear function of a position of input illumination on the LVF.

The method comprises configuring the LVF so a spatial position illuminated on the LVF determines an output wavelength of the LVF.

The method comprises configuring as variable a position of the LVF relative to the light source, wherein the LVF is scanned with the light source.

The method comprises configuring the output of the LVF to include light having a wavelength approximately in a range of 300 nanometers (nm) to 850 nm.

The method comprises configuring the LVF to include a variable pass band filter including a short wave pass component and a long wave pass component.

The short wave pass component includes a first LVF and the long wave pass component includes a second LVF.

The short wave pass component is positioned adjacent the long wave pass component.

The method comprises adjusting a first position of at least one of the short wave pass component and the long wave pass component relative to a second position of the other of the short wave pass component and the long wave pass component, wherein a pass band of the LVF is determined by the first position and the second position.

A position of the SVF in the optical path includes a first region between the light source and the retention device.

A position of the SVF in the optical path includes a second region between the detector and the retention device.

The SVF includes a first SVF component and a second SVF component.

The first SVF component includes a short wave pass component and the second SVF component includes a long wave pass component.

The first SVF component includes a long wave pass component and the second SVF component includes a short wave pass component.

A position of the first SVF component includes a first region of the optical path between the light source and the retention device, and a position of the second SVF component includes the first region.

A position of the first SVF component includes a second region of the optical path between the detector and the retention device, and a position of the second SVF component includes the second region.

A position of the first SVF component includes a first region of the optical path between the light source and the retention device, and a position of the second SVF component includes a second region of the optical path between the detector and the retention device.

The method comprises generating at the detector reflectance data representing a surface of the sample when present.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the spectrometer systems and methods is not intended to be exhaustive or to limit the systems and methods described to the precise form disclosed. While specific embodiments of, and examples for, the spectrometer systems and methods are described herein for illustrative purposes, various equivalent modifications are possible within the scope of other spectrometer systems and methods, as those skilled in the relevant art will recognize. The teachings of the spectrometer systems and methods provided herein can be applied to other processing and measurement systems and methods, not only for the systems and methods described above.

The elements and acts of the various embodiments described above can be combined to provide further embodiments. These and other changes can be made to the spectrometer systems and methods in light of the above detailed description.

In general, in the following claims, the terms used should not be construed to limit the spectrometer systems and methods to the specific embodiments disclosed in the specification and the claims, but should be construed to include all systems and methods that operate under the claims. Accordingly, the spectrometer systems and methods are not limited by the disclosure, but instead the scope of the spectrometer systems and methods is to be determined entirely by the claims.

While certain aspects of the spectrometer systems and methods are presented below in certain claim forms, the inventors contemplate the various aspects of the spectrometer systems and methods in any number of claim forms. Accordingly, the inventors reserve the right to add additional claims after filing the application to pursue such additional claim forms for other aspects of the spectrometer systems and methods.

What is claimed is:

1. A system comprising:
a light source;
a retention device configured to receive and retain a sample for measurement, wherein the sample includes a silicon device;
a detector configured to receive reflected light from the sample, wherein the detector generates a signal representing properties of the silicon device detected using the reflected light, wherein an optical path is defined by the light source, the sample when present, and the detector; and
a spatially variable filter (SVF) positioned in the optical path, wherein the SVF is configured to have spectral properties that vary as a function of illuminated position on the SVF.

2. The system of claim 1, wherein the SVF includes a linear variable filter (LVF), wherein the LVF is configured to have spectral properties that vary linearly with position along a direction of the LVF.

3. The system of claim 2, wherein output illumination of the LVF includes a wavelength that varies as a linear function of a position of input illumination on the LVF.

4. The system of claim 2, wherein the LVF is configured so a spatial position illuminated on the LVF selects an output wavelength of the LVF.

5. The system of claim 2, wherein the LVF comprises a substrate including an interference coating that is graduated along a direction of the LVF.

6. The system of claim 2, wherein a position of the LVF relative to the light source is configured as variable, wherein the LVF is scanned with the light source.

7. The system of claim 2, wherein an output of the LVF includes a series of collimated monochromatic light beams.

8. The system of claim 7, wherein the output of the LVF includes light having a wavelength approximately in a range of 300 nanometers (nm) to 850 nm.

9. The system of claim 2, wherein the LVF is tunable.

10. The system of claim 9, wherein the LVF includes a variable pass band filter comprising a short wave pass component and a long wave pass component.

11. The system of claim 10, wherein the short wave pass component includes a first LVF and the long wave pass component includes a second LVF.

12. The system of claim 10, wherein the short wave pass component is positioned adjacent the long wave pass component.

13. The system of claim 12, wherein a first position of at least one of the short wave pass component and the long wave pass component is adjusted relative to a second position of the other of the short wave pass component and the long wave pass component, wherein a pass band of the LVF is determined by the first position and the second position.

14. The system of claim 13, comprising a translation stage configured to control at least one of the first position and the second position.

15. The system of claim 1, wherein the SVF includes a circularly variable filter (CVF), wherein the CVF is configured to have spectral properties that vary with position along an arc of the CVF.

16. The system of claim 1, wherein the SVF is tunable.

17. The system of claim 1, wherein a position of the SVF in the optical path includes a first region between the light source and the retention device.

18. The system of claim 17, comprising a dichroic filter in the first region.

19. The system of claim 1, wherein a position of the SVF in the optical path includes a second region between the detector and the retention device.

20. The system of claim 19, comprising a dichroic filter in the second region.

21. The system of claim 1, wherein the SVF includes a first SVF component and a second SVF component.

22. The system of claim 21, wherein the first SVF component includes a short wave pass component and the second SVF component includes a long wave pass component.

23. The system of claim 21, wherein the first SVF component includes a long wave pass component and the second SVF component includes a short wave pass component.

24. The system of claim 21, wherein a position of the first SVF component includes a first region of the optical path between the light source and the retention device, and a position of the second SVF component includes the first region.

25. The system of claim 21, wherein a position of the first SVF component includes a second region of the optical path between the detector and the retention device, and a position of the second SVF component includes the second region.

26. The system of claim 21, wherein a position of the first SVF component includes a first region of the optical path between the light source and the retention device.

27. The system of claim 26, wherein a position of the second SVF component includes a second region of the optical path between the detector and the retention device.

28. The system of claim 21, comprising a dichroic filter adjacent at least one of the first SVF component and the second SVF component.

29. The system of claim 1, comprising a dichroic filter.

30. The system of claim 1, comprising an optical objective adjacent the retention device, wherein a position of the optical objective relative to the sample when present is variable.

31. The system of claim 30, wherein the optical objective is configured to at least one of couple light from the light source onto a surface of the sample when present and couple light reflected from the surface to an input of the detector.

32. The system of claim 1, comprising an optical director positioned in the optical path, wherein the optical director is configured to at least one of couple light from the light source to the sample when present and couple reflected light from the sample when present to the detector.

33. The system of claim 32, wherein the optical director comprises at least one of a plurality of mirrors, a beamsplitter, a reflector, and an off-axis reflector.

34. The system of claim 32, wherein the optical director comprises a beamsplitter.

35. The system of claim 1, comprising a condensing device in the optical path between the light source and the retention device.

36. The system of claim 1, comprising a collimator device in at least one of a first region of the optical path between at least one of the light source and the retention device and a second region of the optical path between the detector and the retention device.

37. The system of claim 1, comprising a fiber optic light guide in at least one of a first region of the optical path between at least one of the light source and the retention device and a second region of the optical path between the detector and the retention device.

38. The system of claim 1, comprising an aperture in at least one of a first region of the optical path between at least one of the light source and the retention device and a second region of the optical path between the detector and the retention device.

39. The system of claim 1, wherein the detector comprises a spectrometer.

40. The system of claim 1, wherein the detector comprises a processing device configured to generate reflectance data representing a surface of the sample when present.

41. A system comprising:
a light source;
a retention device configured to receive and retain a sample for measurement, wherein the sample includes a silicon device;
a detector configured to receive reflected light from the sample, wherein the detector generates a signal representing properties of the silicon device detected using the reflected light, wherein an optical path is defined by the light source, the sample when present, and the detector; and
a plurality of spatially variable filters (SVFs) positioned in the optical path, wherein each SVF of the plurality of SVFs is configured to have spectral properties that vary as a function of illuminated position on the SVF.

42. A system comprising:
a light source;

a retention device configured to receive and retain a sample for measurement, wherein the sample includes a silicon device;

a detector configured to receive reflected light from the sample, wherein the detector generates a signal representing properties of the silicon device detected using the reflected light, wherein an optical path is defined by the light source, the sample when present, and the detector; and a spatially variable filter (SVF) including a short wave pass component and a long wave pass component, wherein the SVF is positioned in the optical path, wherein the SVF is configured to have spectral properties that vary as a function of illuminated position on the SVF.

43. A method comprising:

configuring an optical path to couple light between a light source, a sample when present, and a detector, wherein the sample includes a silicon device;

configuring a spatially variable filter (SVF) to pass light having spectral properties that vary as a function of a position of illumination on the SVF;

configuring the optical path to include the SVF in at least one position to control properties of at least one of the light and the reflected light; and configuring the detector to receive reflected light from the sample when present and to generate from the reflected light a signal representing a surface of the sample silicon device when present.

44. The method of claim 43, comprising configuring the SVF to include a linear variable filter (LVF), wherein the LVF is configured to have spectral properties that vary linearly with position along a direction of the LVF.

45. The method of claim 44, comprising configuring the LVF as tunable, wherein output illumination of the LVF includes a wavelength that varies as a linear function of a position of input illumination on the LVF.

46. The method of claim 44, comprising configuring the LVF so a spatial position illuminated on the LVF determines an output wavelength of the LVF.

47. The method of claim 44, comprising configuring as variable a position of the LVF relative to the light source, wherein the LVF is scanned with the light source.

48. The method of claim 44, comprising configuring the output of the LVF to include light having a wavelength approximately in a range of 300 nanometers (nm) to 850 nm.

49. The method of claim 44, comprising configuring the LVF to include a variable pass band filter including a short wave pass component and a long wave pass component.

50. The method of claim 49, wherein the short wave pass component includes a first LVF and the long wave pass component includes a second LVF.

51. The method of claim 49, wherein the short wave pass component is positioned adjacent the long wave pass component.

52. The method of claim 51, comprising adjusting a first position of at least one of the short wave pass component and the long wave pass component relative to a second position of the other of the short wave pass component and the long wave pass component, wherein a pass band of the LVF is determined by the first position and the second position.

53. The method of claim 43, wherein a position of the SVF in the optical path includes a first region between the light source and the retention device.

54. The method of claim 43, wherein a position of the SVF in the optical path includes a second region between the detector and the retention device.

55. The method of claim 43, wherein the SVF includes a first SVF component and a second SVF component.

56. The method of claim 55, wherein the first SVF component includes a short wave pass component and the second SVF component includes a long wave pass component.

57. The method of claim 55, wherein the first SVF component includes a long wave pass component and the second SVF component includes a short wave pass component.

58. The method of claim 55, wherein a position of the first SVF component includes a first region of the optical path between the light source and the retention device, and a position of the second SVF component includes the first region.

59. The method of claim 55, wherein a position of the first SVF component includes a second region of the optical path between the detector and the retention device, and a position of the second SVF component includes the second region.

60. The method of claim 55, wherein a position of the first SVF component includes a first region of the optical path between the light source and the retention device, and a position of the second SVF component includes a second region of the optical path between the detector and the retention device.

61. The method of claim 43, comprising generating at the detector reflectance data representing a surface of the sample when present.

62. A system comprising:

a light source;

a retention device configured to receive and retain a sample for measurement;

a detector configured to receive reflected light from the sample, wherein the detector generates a signal representing the reflected light, wherein an optical path is defined by the light source, the sample when present, and the detector; and a spatially variable filter (SVF) positioned in the optical path and configured to have spectral properties that vary as a function of illuminated position on the SVF, wherein the SVF includes a linear variable filter (LVF) comprising a tunable variable pass band filter including a short wave pass component and a long wave pass component.

63. A system comprising:

a light source;

a retention device configured to receive and retain a sample for measurement;

a detector configured to receive reflected light from the sample, wherein the detector generates a signal representing the reflected light, wherein an optical path is defined by the light source, the sample when present, and the detector; and a spatially variable filter (SVF) positioned in the optical path, wherein the SVF includes a first SVF component and a second SVF component, wherein the SVF is configured to have spectral properties that vary as a function of illuminated position on the SVF.

* * * * *